US006473174B1

(12) United States Patent
Ballast et al.

(10) Patent No.: US 6,473,174 B1
(45) Date of Patent: Oct. 29, 2002

(54) RESIST REMOVAL MONITORING BY RAMAN SPECTROSCOPY

(75) Inventors: Lynette K. Ballast; Mark R. Breen, both of Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 99 days.

(21) Appl. No.: 09/653,435

(22) Filed: Sep. 1, 2000

(51) Int. Cl.$^7$ .............................. G01J 3/44; G01N 21/00
(52) U.S. Cl. ...................... 356/301; 356/237.4
(58) Field of Search ................. 356/300, 301, 356/306, 326, 337, 338, 237.1–237.5; 600/475, 477, 310, 318; 606/2–4, 10; 250/559.01

(56) References Cited

U.S. PATENT DOCUMENTS 6,205,354 B1 * 3/2001 Gellermann et al. ........ 600/477

OTHER PUBLICATIONS

U.S. application No. 09/428,147, Pickelsimer et al., filed Oct. 27, 1999.
University of Missouri Kansas City; *Raman Scattering: Classical Definition*; http://cctr.umkc.edu/www/w3/dept/physics/ramanderivation.htm.; pp. 1–2; Jul. 6, 2000; US.
University of Utah Department of Electrical Engineering; *Raman Spectroscopy*; http://www.elen.utah.edu/~devans/raman/report2f.htm; p.1; Jul. 6, 2000; US.
University of Michigan *Raman Spectroscopy Explained*; http://www~personal.umich.edu:80/~jshaver/virtual/explain.html; p. 1; Jul. 6, 2000; US.
Brian M. Tissue; *Raman Spectroscopy*; http://www.scimedia.com/chem~ed/spec/vib/raman.htm; p. 2; Sep. 12, 1996; US.

* cited by examiner

*Primary Examiner*—Michael P. Stafira
(74) *Attorney, Agent, or Firm*—Timothy M. Honeycutt

(57) ABSTRACT

Various methods of inspecting a workpiece for residue are provided. In one aspect, a method of inspecting a workpiece for carbon residue includes directing coherent radiation at the workpiece to produce Rayleigh scattered radiation and Raman scattered radiation. The Rayleigh scattered radiation is filtered out. A spectrum for the Raman scattered radiation is detected and compared with a known Raman spectrum for carbon. Wafers may be inspected for residues, such as graphitic carbon, in a non-destructive way and without pump down. Deficiencies in resist stripping may be quickly identified.

25 Claims, 2 Drawing Sheets

RESIST REMOVAL MONITORING BY RAMAN SPECTROSCOPY

BACKGROUND OF THE INVENTION

1. Field of the Invention

This invention relates generally to semiconductor processing, and more particularly to a method of inspecting a semiconductor workpiece for carbon-based films using Raman spectroscopy.

2. Description of the Related Art

Accurate and reliable defect inspection is vital to successful semiconductor fabrication. Microelectronic circuit structures may be highly sensitive to contamination by particulates introduced by various semiconductor processing tools and to the various deleterious effects associated with unwanted residual films left over after semiconductor processing steps. Most semiconductor chip fabrication techniques involve the sequential application of films of various compositions on a silicon wafer or substrate. The successful application of the stacked films often requires a relatively pristine underlying surface upon which each successive layer is formed. However, the presence of an unwanted residual film on the underlying layer may cause the overlying film to later delaminate and lead to device failure. Examples of unwanted residual films remaining after a given semiconductor processing step are legion. One example involves the formation of residual graphitic carbon following carbon-based photoresist stripping. Carbon-based photoresists are commonly used as masking materials for etching, ion implantation and various other semiconductor processing steps.

A given process for fabricating an integrated circuit may entail scores of different photomask steps, each involving the application and removal of a resist film. In many modern semiconductor fabrication processes, mask removal involves a plasma based removal or ashing step that is followed by some type of aqueous acidic or solvent cleaning process, such as a so-called RCA solvent cleaning. The plasma process converts some of the carbon present in the photoresist into graphitic-form carbon. Whether in graphite form or not, the resist strip process may not completely remove the carbon based resist material and thus leave a graphitic carbon residue on the wafer. It is highly desirable to be able to detect the presence of a carbon based residue film following resist strip and to be able to discriminate between graphitic form carbon and non-graphitic-form carbon. The presence of graphitic-form carbon indicates a possible shortcoming in the ashing and/or the solvent resist stripping process. Non-graphitic carbon may be present in the form of various hydrocarbon complexes and may be indicative of contamination from processing chamber walls or plumbing or from residual compounds left over from anisotropic etching processes utilizing fluorocarbons.

Various techniques have been used as a means of detecting the presence of carbon-based residual films on semiconductor wafers. Scanning electron microscopy ("SEM") has been used as a means of identifying the presence of thin films in general, and attempts have been made to apply it to the identification of carbon based residues. Many SEM instruments are provided with an electron disperse x-ray spectrometer ("EDX") that can identify the elemental composition of a contaminant film. However, SEM does not necessarily provide an exact identification of the chemical composition of the material inspected. For example, SEM with EDX generally cannot distinguish allotropic species. Furthermore, a time-consuming vacuum pump-down is required prior to the performance of the SEM scan.

Time of flight secondary ion beam spectroscopy ("TOF SIMS") has also been used as a method of inspecting for carbon based residues. However, TOF SIMS is destructive of the scanned structure, and like SEM, requires vacuum conditions and the associated pump down times.

The present invention is directed to overcoming or reducing the effects of one or more of the foregoing disadvantages.

SUMMARY OF THE INVENTION

In accordance with one aspect of the present invention, a method of inspecting a workpiece for carbon residue is provided. The method includes directing coherent radiation at the workpiece to produce Rayleigh scattered radiation and Raman scattered radiation. The Rayleigh scattered radiation is filtered out. A spectrum for the Raman scattered radiation is detected and compared with a known Raman spectrum for carbon.

In accordance with another aspect of the present invention, a method of inspecting a semiconductor wafer for carbon-based photoresist residue is provided. The method includes directing coherent radiation at the wafer to produce Rayleigh scattered radiation and Raman scattered radiation. The Rayleigh scattered radiation is filtered out. A spectrum for the Raman scattered radiation is detected and compared with a known Raman spectrum for graphitic carbon.

In accordance with another aspect of the present invention, a method of processing a semiconductor workpiece that has a carbon-based resist film is provided. The method includes stripping the carbon-based resist film and inspecting the workpiece for carbon-based residue by directing coherent radiation at the workpiece to produce Rayleigh scattered radiation and Raman scattered radiation. The Rayleigh scattered radiation is filtered out and a spectrum for the Raman scattered radiation is detected and compared with a known Raman spectrum for carbon.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
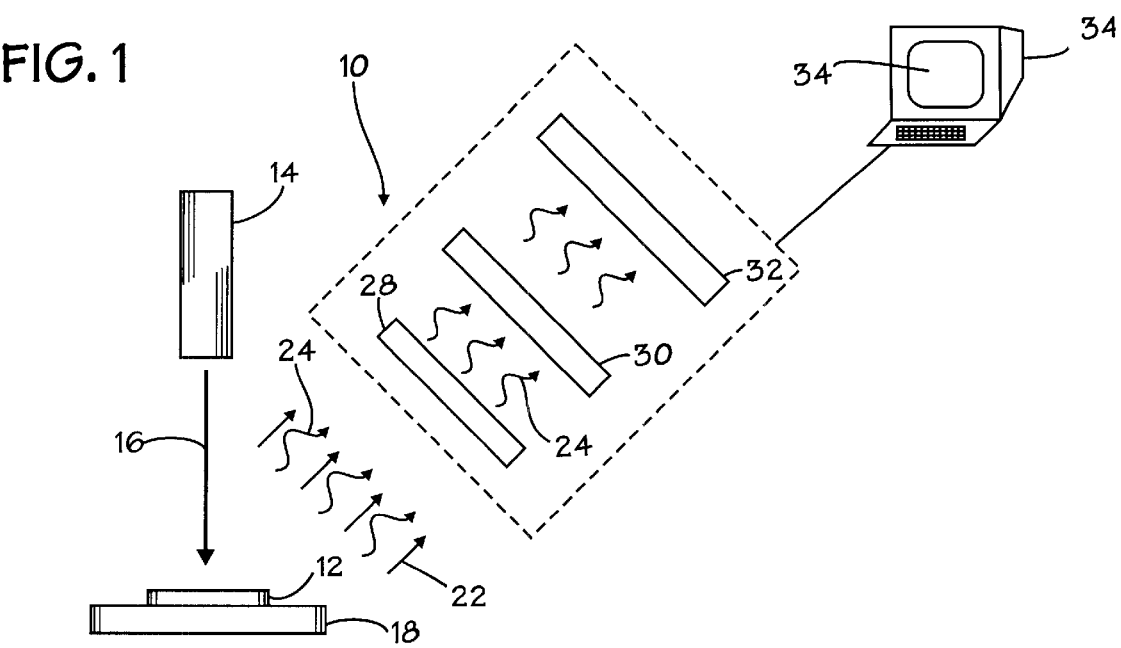
FIG. 1 is a simplified schematic view of an exemplary embodiment of a Raman spectroscopy system in accordance with the present invention.

In the drawings described below, reference numerals are generally repeated where identical elements appear in more than one figure. FIG. 1 illustrates a simplified schematic view of an exemplary embodiment of a Raman spectroscopy system 10 (hereinafter "system 10") for inspecting a workpiece 12 for the presence of various residual films and particulates. In the illustrated embodiment, the workpiece 12 is a semiconductor wafer of the type commonly used to fabricate integrated circuits. However, other types of workpieces may be inspected as well. The system 10 includes a source 14 of coherent electromagnetic radiation that is capable of directing an incident beam 16 toward the workpiece 12 in order to produce scattered radiation 17 that may be analyzed. The coherent radiation source 14 may be a laser or other source of coherent electromagnetic radiation. In an exemplary embodiment, the coherent radiation source 14 is a laser capable of generating coherent radiation in the 244 to 780 nm range. However, the skilled artisan will appreciate that the term "laser" is intended to encompass radiation inside and outside the visible light spectrum. A variety of lasers may be used, such as, for example, argon-ion lasers and high-repetition-rate excimer-laser-pumped pulsed dye lasers, to name just a few.

The workpiece 12 is seated on a carrier or stage 18 that may be stationary or movable as desired. The incident beam 16 is scanned across the surface of the workpiece 12, either by movable optics (not shown), or by movement of the stage 18 or by a combination of the two. As noted above, the incident beam 16 is directed at the workpiece 12 to generate scattered radiation 17. The scattered radiation 17 consists of a plurality of elastically scattered light rays or photons 22 and a plurality of inelastically scattered light rays or photons 24. The elastically scattered photons 22 will generally have the same frequency as the incident beam 16. However, the inelastically scattered photons 24 will have a shifted frequency due to inelastic interactions between the incident beam 16 and chemical bonds within the impacted surface of the workpiece 12. The elastically scattered photons are referred to as Rayleigh scattered light while the inelastically scattered photons 24 are referred to as Raman scattered light. The spectrum of the Raman scattered photons provides a unique signature of the composition and various other physical properties of the impacted surface of the workpiece 12. Thus, the Raman spectrum may be used to discriminate different materials on the workpiece 12.

The Raman spectrum is gathered by passing the scattered light 17 into an analyzer 26 that includes a filter 28, a diffraction grating 30 and a charge couple device ("CCD") detector 32. The filter 28 is designed to filter out the Rayleigh scattered photons 22 and permit only the Raman scattered photons 24 to pass through the diffraction grating 30. The diffraction grating 30 generates an intensity pattern which is detected by the CCD detector 32. The output of the CCD device 32 is sent to a computer analyzer 34 that may include a human readable display 36 as shown. The computer analyzer 34 is operable to receive the output signal from the CCD device 32 and generate a Raman spectrograph from that output. The Raman spectrograph will provide a unique signature for the scanned portion of the workpiece 12 and thus provide the identity of the material scanned. The Raman spectrograph may be compared with various known Raman spectrographs for various materials that may be stored in a library within the computer analyzer 32 or in another storage medium.

As noted above, identifying carbon based residues, such as those created by plasma based resist stripping techniques, and in particular discriminating graphitic carbon from non-graphitic carbon is a difficult task. Some semiconductor processing films are particularly sensitive to carbon contamination, such as, for example copper conductor films and gate oxides.

Figure 2:
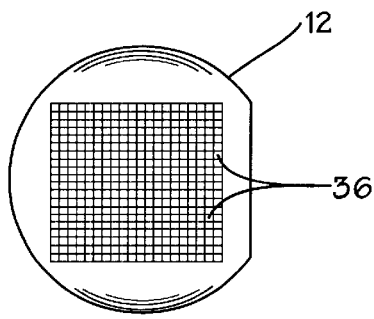
FIG. 2 is an overhead view of a semiconductor workpiece inspected by the Raman spectroscopy system of FIG. 1 in accordance with the present invention.
Figure 3:
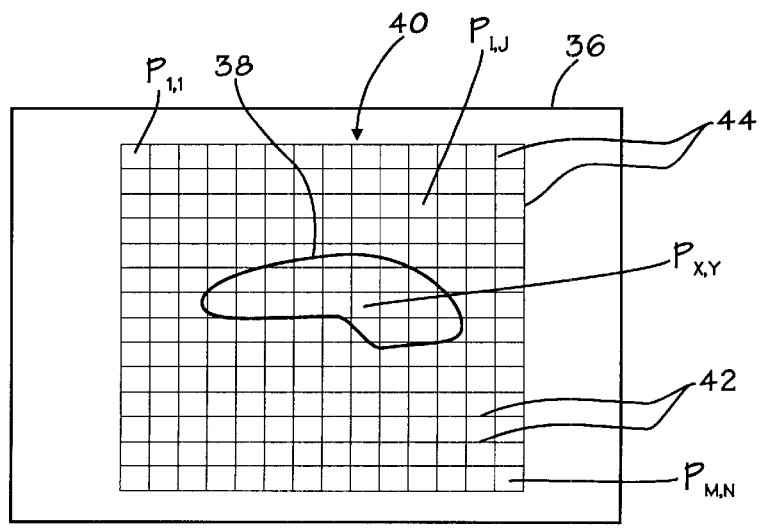
FIG. 3 is a magnified view of a selected portion of the semiconductor workpiece shown in FIG. 2 in accordance with the present invention.

An illustrative embodiment of a method in accordance with the present invention utilizes the Raman spectroscopy system 10 disclosed in FIG. 1 to detect graphitic carbon residues on the workpiece 12. The method may be understood by referring now to FIGS. 1, 2,3 and 4. FIG. 2 is an overhead view of the workpiece 12. For the purpose of illustration, the workpiece 12 is provided with a plurality of integrated circuits or die 36. FIG. 3 is a magnified view of one of the die 36. To better illustrate the method, a carbon-based resist film (not shown) has been patterned on the die 36 and thereafter plasma stripped. A hypothetical graphitic carbon residue 38 of the type that may be left over following stripping of organic resist is shown on the upper surface of the die 36.

The die 36 is scanned with the incident radiation 16 and the Raman spectrum scattering therefrom may be analyzed for carbon residue. The scan may be performed according to a grid pattern 40 that is digitally overlaid on the die 36 by the system 10. The grid 40 consists of a plurality of intersecting horizontal lines 42 and vertical lines 44, which define a plurality of pixels, $P_{1,1} \ldots P_{M,N}$. In this way, the incident beam 16 shown in FIG. 1 may be scanned across the surface of the workpiece 12 and the Raman scattering sensed by the CCD device 32 may be associated with given and precisely known pixel locations on the workpiece 12, such as, for example, the two pixel locations $P_{X,Y}$ and $P_{I,J}$. In an exemplary embodiment, the Raman spectroscopy inspection of the workpiece 12 is carried out by laser scanning via a raster scan of the various pixels $P_{1,1} \ldots P_{M,N}$. However, other well known scanning patterns may be used.

Figure 4:
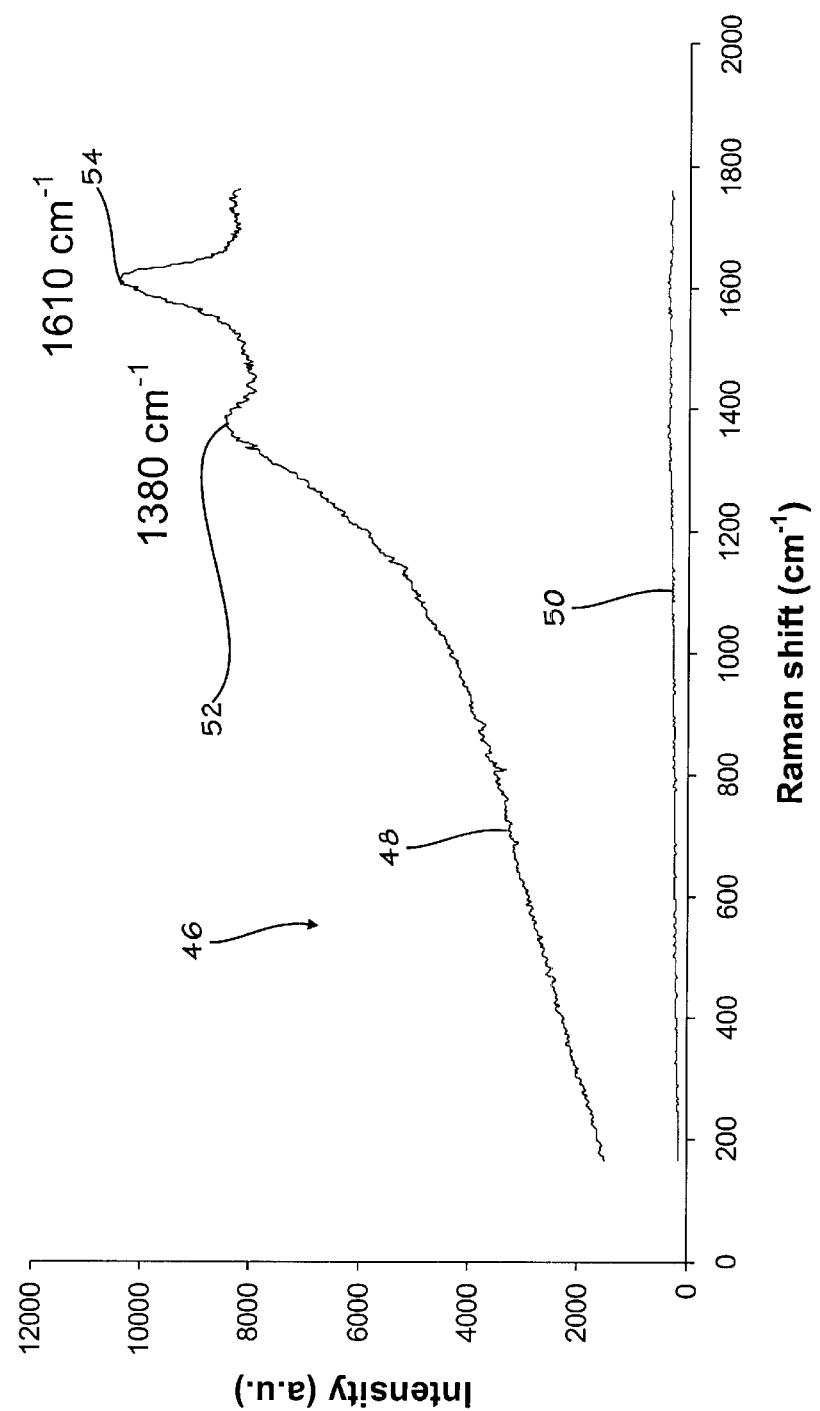
FIG. 4 is an exemplary Raman spectrum plot for two points on the semiconductor workpiece shown in FIG. 2 in accordance with the present invention.

An exemplary Raman spectrograph 46 associated with the pixels $P_{X,Y}$ and $P_{I,J}$ is depicted in FIG. 4. In the illustrated embodiment, the spectrograph 46 includes plots 48 and 50 of Raman shift versus relative intensity corresponding respectively to the pixel locations $P_{X,Y}$ and $P_{I,J}$. The plots 48 and 50 may be compared by the analyzer 32 shown in FIG. 1 with known Raman spectra for various materials, such as graphitic carbon, oxide, silicon or others. If desired, the analyzer 32 may also generate a visual output of the plot of FIG. 4 in human readable form on the display 34. The skilled artisan will appreciate that the Raman spectra may be presented in a variety of ways. For example, the specific number of Raman shift units or wave numbers presented in the plot 46 will depend upon the angle at which the Raman scattered photons 24 strike the diffraction grating as well as the number of slits or grooves in the diffraction grading 28 (See FIG. 1).

The plot 48 corresponding to the pixel location $P_{X,Y}$, and thus the resist residue 38, presents two distinct peaks 52 and 54 that correspond to Raman shifts of 1380 $cm^{-1}$ and 1610 $cm^{-1}$ respectively. However, the plot 50 corresponding to the pixel location $P_{I,J}$ outside of the residue 38 is relatively flat, indicating an absence of carbon. The peaks 52 and 54 indicate the presence of graphitic carbon, and thus suggest the potential need for corrections to be made in the resist strip process. If, however, the plots 48 and 50 indicated the presence of some other type or types of materials, then other corrective actions may be explored in the prior processing steps if deemed appropriate.

In an exemplary embodiment, a Renishaw Raman spectrometer system is used in conjunction with a Leica INF 3000 review station. However, the skilled artisan will appreciate that the particular tools and instrumentation used are largely matters of design discretion.

The skilled artisan will appreciate that the process of the present invention provides for rapid and accurate inspection of wafers and other workpieces for carbon-based residues. The method is non-destructive and does not require high vacuums conditions the attendant lengthy pump down times. Accordingly, integration directly into semiconductor fabrication lines is envisioned. Because graphitic carbon presents a relatively large Raman cross-section, such films may be detectable down to the 1E12 atoms/cm$^{-2}$ level. The method is accordingly well suited to identifying post-resist strip films. The method may be applied to a wide variety of underlying films. Examples include, silicon nitride, silicon oxynitride, aluminum and polymers, such as SiLK®, to name just a few.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives failing within the spirit and scope of the invention as defined by the following appended claims.

What is claimed is:

1. A method of inspecting a semiconductor workpiece for carbon residue, comprising:

directing coherent radiation at the semiconductor workpiece to produce Rayleigh scattered radiation and Raman scattered radiation;

filtering out the Rayleigh scattered radiation;

detecting a spectrum for the Raman scattered radiation; and comparing the detected spectrum with a known Raman spectrum for carbon.

2. The method of claim 1, wherein the coherent radiation falls within a visible light spectrum.

3. The method of claim 2, wherein a laser is used to direct the coherent radiation at the semiconductor workpiece.

4. The method of claim 1, wherein the semiconductor workpiece comprise an oxide film and the coherent radiation is directed at the oxide film.

5. The method of claim 1, wherein the semiconductor workpiece comprises a copper film and the coherent radiation is directed at the copper film.

6. The method of claim 1, wherein the comparison of the detected spectrum with a known Raman spectrum for carbon is performed by a computer.

7. The method of claim 6, wherein the known Raman spectrum for carbon is retrieved from a database.

8. The method of claim 1, wherein the semiconductor workpiece comprises a film of oxide, copper, silicon nitride, silicon oxynitride, aluminum or a polymer and the coherent radiation is directed at the film of oxide, copper, silicon nitride, silicon oxynitride, aluminum or a polymer.

9. A method of inspecting a semiconductor wafer for carbon-based photoresist residue, comprising:

directing coherent radiation at the wafer to produce Rayleigh scattered radiation and Raman scattered radiation;

filtering out the Rayleigh scattered radiation;

detecting a spectrum for the Raman scattered radiation; and comparing the detected spectrum with; a known Raman spectrum for graphitic carbon.

10. The method of claim 9, wherein the coherent radiation falls within a visible light spectrum.

11. The method of claim 10, wherein a laser is used to direct the coherent radiation at the wafer.

12. The method of claim 9, wherein the wafer comprises an oxide film and the coherent radiation is directed at the oxide film.

13. The method of claim 9, wherein the wafer comprises a copper film and the coherent radiation is directed at the copper film.

14. The method of claim 9, wherein the wafer comprises a film of oxide, copper, silicon nitride, silicon oxynitride, aluminum or a polymer and the coherent radiation is directed at the film of oxide, copper, silicon nitride, silicon oxynitride, aluminum or a polymer.

15. The method of claim 9, wherein the comparison of the detected spectrum with a known Raman spectrum for graphitic carbon is performed by a computer.

16. The method of claim 15, wherein the known Raman spectrum for graphitic carbon is retrieved from a database.

17. A method of processing a semiconductor workpiece having a carbon-based resist film, comprising:

stripping the carbon-based resist film; and inspecting the workpiece for carbon-based residue by directing coherent radiation at the workpiece to produce Rayleigh scattered radiation and Raman scattered radiation, filtering out the Rayleigh scattered radiation, detecting a spectrum for the Raman scattered radiation, and comparing the detected spectrum with a known Raman spectrum for carbon.

18. The method of claim 17, wherein the carbon-based resist film is stripped by plasma stripping.

19. The method of claim 17, wherein the coherent radiation falls within a visible light spectrum.

20. The method of claim 19, wherein a laser is used to direct the coherent radiation at the workpiece.

21. The method of claim 17, wherein the workpiece comprises an oxide film and the coherent radiation is directed at the oxide film.

22. The method of claim 17, wherein the workpiece comprises a copper film and the coherent radiation is directed at the copper film.

23. The method of claim 17, wherein the workpiece comprises a film of oxide, copper, silicon nitride, silicon oxynitride, aluminum or a polymer and the coherent radiation is directed at the film of oxide, copper, silicon nitride, silicon oxynitride, aluminum or a polymer.

24. The method of claim 17, wherein the comparison of the detected spectrum with a known Raman spectrum for graphitic carbon is performed by a computer.

25. The method of claim 24, wherein the known Raman spectrum for graphitic carbon is retrieved from a database.

* * * * *